(12) United States Patent
Morrow et al.

(10) Patent No.: US 6,604,051 B1
(45) Date of Patent: Aug. 5, 2003

(54) SYSTEM AND METHOD TO DETERMINE THERMOPHYSICAL PROPERTIES OF A MULTI-COMPONENT GAS

(75) Inventors: Thomas B. Morrow, San Antonio, TX (US); Kendricks A. Behring, II, Torrance, CA (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 09/550,431

(22) Filed: Apr. 17, 2000

(51) Int. Cl.$^7$ .................................................. G01N 9/00
(52) U.S. Cl. ........................................................ 702/24
(58) Field of Search .................. 702/150, 24; 73/24.05, 73/25.01, 23, 61, 861, 24, 596, 600, 579

(56) References Cited

U.S. PATENT DOCUMENTS

| | | | |
|---|---|---|---|
| 4,596,133 A | | 6/1986 | Smalling et al. .................. 73/24 |
| 5,486,107 A | | 1/1996 | Bonne .......................... 431/12 |
| 5,537,854 A | | 7/1996 | Phillips et al. ............. 73/24.01 |
| 5,932,793 A | * | 8/1999 | Dayton et al. ............. 73/24.05 |
| 6,047,589 A | | 4/2000 | Hammond et al. ........ 73/24.01 |
| 6,065,328 A | * | 5/2000 | Dayton et al. ............. 73/25.01 |
| 6,209,387 B1 | * | 4/2001 | Savidge ..................... 73/24.05 |
| 6,286,360 B1 | * | 9/2001 | Drzewiecki ................ 73/24.01 |

FOREIGN PATENT DOCUMENTS

| | | | |
|---|---|---|---|
| DE | 198 23 193 A1 | 11/1999 | ............ G01N/9/00 |
| EP | 1 063 525 A2 | 7/1999 | .......... G01N/33/22 |
| EP | 0 939 317 A2 | 9/1999 | .......... G01N/33/22 |
| EP | 0 959 354 A2 | 11/1999 | .......... G01N/33/22 |
| WO | WO 93/08457 | 4/1993 | ............ G01N/9/00 |
| WO | WO 99/10740 | 3/1999 | .......... G01N/33/22 |

OTHER PUBLICATIONS

PCT/US01/12217 Search Report, Mailed Nov. 13, 2001.
International Preliminary Examination Report PCT/US01/12217 Jul. 8, 2002.
Wild, K.R., "Controlling Processes that are Sensitive to Natural Gas Quality", presented at the 21st World Gas Conference, Nice France, Jun. 6–9, 2000.

* cited by examiner

Primary Examiner—John Barlow
Assistant Examiner—Tung Lau
(74) Attorney, Agent, or Firm—Baker Botts L.L.P.

(57) ABSTRACT

A system and method to characterize natural gas hydrocarbons using a single inferential property, such as standard sound speed, when the concentrations of the diluent gases (e.g., carbon dioxide and nitrogen) are known. The system to determine a thermophysical property of a gas having a first plurality of components comprises a sound velocity measurement device, a concentration measurement device, and a processor to determine a thermophysical property as a function of a correlation between the thermophysical property, the speed of sound, and the concentration measurements, wherein the number of concentration measurements is less than the number of components in the gas. The method includes the steps of determining the speed of sound in the gas, determining a plurality of gas component concentrations in the gas, and determining the thermophysical property as a function of a correlation between the thermophysical property, the speed of sound, and the plurality of concentrations.

28 Claims, 2 Drawing Sheets

SYSTEM AND METHOD TO DETERMINE THERMOPHYSICAL PROPERTIES OF A MULTI-COMPONENT GAS

GOVERNMENT LICENSE RIGHTS

The U.S. Government has a paid-up license in this invention and the right in certain circumstances to require the patent owner to license others on reasonable terms as provided for by the terms of Contract No. DE-FC21-96MC33033 for the U.S. Department of Energy.

BACKGROUND OF THE INVENTION

1. Field of the Invention

This invention relates to the field of measuring thermophysical properties of gases, and more particularly, to the determination of thermophysical gas properties using gross inferential properties and empirical correlations.

2. Description of the Related Art

Current technology provides two approaches to energy flow rate measurement for natural gas. The first requires a composition assay and a flow rate measurement. The composition assay allows calculating the heating value of the gas, and is also required to calculate selected gas properties (e.g., gas density) needed to determine energy flow rates. The second approach measures gas density and heating value directly, using special instrumentation, and requires no composition assay. Each approach can be further divided into sub-categories, based on the equipment used to effect measurements.

Gas chromatographs measure gas composition by separating the gas to be measured into pure components, and then detecting the concentration of each component separately. The process includes collecting a gas sample from the pipeline, and injecting it into one or more columns. After separation by the columns, the magnitude of pure gas component concentrations are sensed by various detectors. Gas chromatographs are typically quite expensive, require several minutes to effect an analysis, and require specially-prepared gas composition standards to calibrate the detectors for each targeted gas component. After the cost of instrument housing, calibration standards, sampling systems, and other accessories are added together, the total cost of purchase and maintaining a gas chromatograph system in the field is simply impractical for gas suppliers dealing in volumes of less than one million scfd.

Calorimeters provide a way to directly measure heating value, because they burn a gas sample and measure the heat generated. However, commercially available calorimeters measure standard volumetric heating value at low pressure, and not at flowing temperature and pressure. Thus, some measurement of gas density is also required to calculate the energy flow rate, even for volume-based meters. Reconditioned calorimeters can be purchased for approximately $10,000 to $20,000, but are difficult to procure as new items.

Another method of measurement involves the use of an inferential calorimeter, which infers heating value from stoichiometric combustion properties. However, a densitometer is still required to determine the energy flow rate for a volume-based meter. Periodic calibration is required using pure methane gas having a known heating value. To reach the required stoichiometric condition in one such device, the fuel flow rate (which is correlated to heating value) must be changed to accommodate rich gas (i.e., high heating value) and lean gas (i.e., lower heating value). Prices for these instruments also range from approximately $10,000 to $20,000.

There are also other devices, such as the PMI system manufactured by Badger Meter, Inc., which provide real-time, direct measurement of natural gas energy flow. Thus, these systems are not limited to measuring the energy content of the gas. However, such systems are used in conjunction with flow meters and sampling lines, such that the value measured must be scaled up to the pipeline rate using differential pressure measurements across the pipeline and sampling line orifices so as to exploit the thermodynamic similarity between the gas in the pipeline and the sampling line orifices. However, as a practical matter, the mini-orifice used is not geometrically similar to the actual pipeline orifice, and the flow characteristics between the two may be quite different.

Attempts have also been made to correlate standard volumetric heating value to the speed of sound in gas. However, there is no published evidence of attempts to correlate sound speed with the actual volumetric heating value, which depends on the gas composition, flow temperature, and pressure. Thus, correlation requires the use of known diluent concentrations, which may be unavailable in the field.

Other correlation attempts include measurement of gas dielectric constants, thermal conductivity, specific heat and other properties. While the results are encouraging, error values may be as high as 3.5% and no published data exists to verify measurement and prediction of the actual volumetric heating value from sensed properties at various operating pressures.

In summary, the state of the art in natural gas flow rate and energy flow rate measurement requires determination of a detailed flowing gas composition analysis. The composition assay is then used to calculate gas properties needed to determine the energy flow rate for a particular pipeline, and currently requires the application of an expensive and technically sophisticated instrument, in the form of a gas chromatograph.

A low-cost, easy-to-maintain apparatus and method are therefore required to facilitate accurate energy flow rate determinations for natural gas and other fluids. The need for such device increases as a result of industry deregulation, which has introduced widely-varying compositions of gas into natural gas pipelines.

SUMMARY OF THE INVENTION

The system and method of the present invention provide for determination of thermophysical properties of multi-component gases based on the determination of two quantities: the speed of sound in the gas and the concentration of a plurality of components comprising the gas. As a specific example, the concentration of carbon dioxide and nitrogen are determined, along with the speed of sound in the gas, to determine a thermophysical property (e.g. the Mixture Molar Ideal Gross Heating Value) as a function of an empirical correlation between the thermophysical property, the speed of sound, the concentration of carbon dioxide, and the concentration of nitrogen in the gas. For greater accuracy, the speed of sound may be determined at a fixed temperature and pressure of the gas.

Depending on the gas components for which the concentration is determined, various thermophysical properties can be determined more or less accurately. For example, the Mixture Molar Ideal Gross Heating Value, the Mixture Molecular Weight, the Mass-Based Heating Value, and the Density of the gas can all be determined within about ±0.02% of selected model values by implementing the system and method of the present invention.

The speed of sound and concentration of gas components may be determined directly (e.g., via measurement), or indirectly. For example, the concentration of a particular gas component may be determined by correlating a thermodynamic property for the selected component with one or more directly measurable inferential properties of the component.

The invention also includes a method to determine a gas thermophysical property comprising the steps of determining a speed of sound in the gas, determining a plurality of gas component concentrations which make up a subset of the total number of components comprising the gas, and then determining the selected thermophysical property as a correlation function between the thermophysical property, the speed of sound in the gas, and the plurality of gas component concentrations, wherein the number of component concentrations is less than the total number of total components comprising the gas. Examples of component concentrations which may require determination include those for carbon dioxide and nitrogen; the speed of sound may be measured at a fixed temperature and pressure for greater accuracy.

As is the case for the apparatus, the method may be used to determine the Mixture Molar Ideal Gross Heating Value, the Mixture Molecular Weight, the Mass-Based Heating Value, or the Density of the gas. The speed of sound and component concentrations may be measured directly, or indirectly. Thus, the concentrations may also be determined by correlating a thermodynamic property of selected components with one or more directly measurable inferential properties of the same components.

BRIEF DESCRIPTION OF THE FIGURES

A more complete understanding of the structure and operation of the present invention may be had by reference to the following detailed description when taken in conjunction with the accompanying drawings, wherein.

DETAILED DESCRIPTION OF THE PREFERRED EMBODIMENT

The goal of improving energy measurement technology may be approached by refining traditional gas chromatography equipment and measurement methods, or by exploiting a different approach that overcomes the inherent disadvantages of composition assay investigation. Even if the cost of traditional gas chromatographs is lessened by producing less expensive component elements (e.g., detectors, injectors, switching valves, etc.), the process of gas separation remains. Thus, a different approach has been taken, as described hereinbelow.

Natural gas is largely composed of paraffin hydrocarbons having a similar molecular structure. Exploiting the resulting interdependence of properties allows characterizing the hydrocarbon energy in gas without a detailed composition assay. First, the diluent concentrations (e.g., predominantly nitrogen and carbon dioxide) are quantified, since these have no energy content. The concentrations may be measured with approximate accuracy, as these components account for only a small fraction of the whole natural gas mixture. Second, the remaining hydrocarbon gas component (i.e., the majority of the gas mixture) can be characterized by inferential properties, without differentiation of species. However, if only one diluent component concentration is known (e.g., carbon dioxide), then a second diluent-sensitive inferential property may be required to complete the characterization of hydrocarbon energy in a particular gas sample.

By measuring inferential properties with less costly sensors, and determining natural gas characterization correlations between properties required for energy measurement, a dramatic cost savings over traditional gas chromatography installations can be achieved. For the purpose of describing the present invention, three inferential properties were selected in an exemplary fashion. These are: the speed of sound at 60° F. and 14.73 psia (i.e., standard temperature and pressure), carbon dioxide concentration, and nitrogen concentration.

Figure 1:
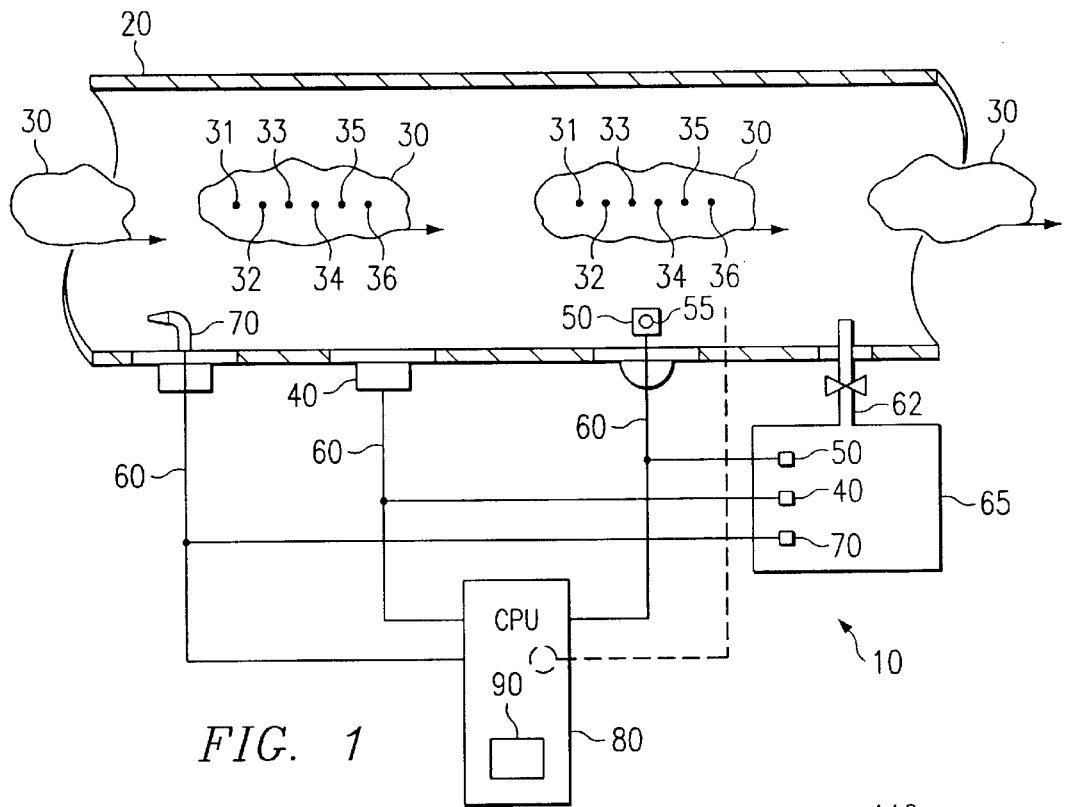
FIG. 1 is a block diagram of the apparatus of the present invention.

Turning now to FIG. 1, the apparatus of the present invention can be seen. The system 10 for determining thermophysical properties of a gas is typically installed on a gas pipeline. The pipe 20 is shown in a cut-away view carrying a multi-component gas 30 (or, using alternative terminology, a gas having a plurality of components 30). Typically, such components include nitrogen 31, carbon dioxide 32, methane 33, ethane 34, propane 35, and heavier hydrocarbons 36, each component existing within the gas 30 in varying proportions.

The system includes a sound velocity measurement device 40 adapted to measure the speed of sound in the gas 30. This device is preferably an inexpensive ultrasonic flow meter, such as those produced by Siemens for residential applications in the European gas market, e.g. the Siemens E6 domestic gas meter. In addition, any of the following meters are suitable for use as a sound velocity measurement device 40 in the gas 30: Daniel Senior Sonic, Junior Sonic, and UltraTap ultrasonic flow meters; the Smith Meter Kongsberg MPU 1200 ultrasonic flow meter; the Panametrics Ultrasonic Transit-Time flow meter; and the Instromet Q Sonic -2S, -3S, and -5S ultrasonic flow meters. The sound velocity measurement device 40 may also comprise an array of ultrasonic sensors and associated electronics configured specifically to measure the speed of sound, as is well known in the art.

Also comprising an element of the preferred embodiment is a concentration measurement device 50 adapted to determine the concentration of a plurality of components comprising the gas 30. The concentration measurement device 50 can include a commercial, non-dispersive infrared sensor, which may be similar to or identical to the Vaisala model GMM11, which measures the concentration of carbon dioxide using infrared energy absorption. Other suitable instruments which may comprise the device 50 and which can be used to determine component concentrations include sensors or meters to directly measure the concentration of nitrogen, carbon dioxide, and/or other components.

As an alternative approach, the concentration measurement device 50 may be used to determine a gas concentration inferentially, in combination with measurements of sound speed and another gas component concentration. Examples include the inferential determination of $N_2$ by any of the following methods: measuring the sound speed at two different pressures and temperatures, measuring heat dissipation and temperature rise in a container having a fixed volume, measuring heat dissipation and temperature rise in a gas stream flowing at a constant rate, or independently measuring the gas density.

The sound velocity measurement device 40 and the concentration measurement device 50 are typically connected so as to be in electrical communication with the processor 80 using cables 60. A correlation device 55 may also comprise a part of the concentration measurement device, or reside as an independent correlation device 55 outside the measurement device 50, such as in the processor 80. The correlation device 55 may be incorporated as a software module within the processor 80, or as a separate hardware module, such as a Digital Signal Processor (DSP) or some other computational device dedicated to effecting the correlation calculations described hereinafter. That is, the computational load on the processor 80 may be divided between the processor 80 and the correlation device 55. However, in certain applications, there is no need for this type of division, and the processor 80 may be suitable for gathering data from the various sensors and making the correlation computations necessary to carry out the method of the present invention. In conjunction with the flow meter 70, which may be an ultrasonic, orifice, turbine, rotary, Coriolis, or diaphragm type, the gas flow rate and energy flow rate may be determined using only the speed of sound, carbon dioxide concentration, nitrogen concentration, temperature, and pressure. Typically, the processor 80 will have a memory 90 for storing the results of sensor measurements, programming information, and calculation results for chemical properties of the gas 30.

As can be seen in FIG. 1, the measurements of concentration and speed of sound can be made within the pipe 20 at flowing temperature and pressure. Alternatively, the measurements can be made within a gas sample, outside of the pipe, held in a sample chamber 65, for example. In this case, the gas may be sampled from within the pipe 20 by using a sample tube 62 which directs the gas sample into a sample chamber 65. Thus, any one or more of the measurements noted above can be made within the sample chamber 65 using the concentration measurement device 50, the sound velocity measurement device 40, and/or the natural gas flow meter 70. Measurements of any of these properties may be made within the pipe 20, within the sample chamber 65, or from a combination of the two locations. A preferred embodiment makes use of an existing ultrasonic flow meter 40 to measure the sound speed in the pipeline 20 at the flowing gas temperature and pressure, and a gas sample stream drawn off of the pipeline 20 through a sample tube 62 to measure the nitrogen and carbon dioxide concentrations.

Natural gas flow meters 70 may be generally classified as volume-based (ultrasonic, turbine, rotary, diaphragm, etc.), differential-based (orifice, annular, V-cone, etc.), and mass-based (Coriolis, thermal-mass, etc.). Any of these meters 70 may be used for energy measurement, but each meter classification requires the determination of different properties to complete the energy flow rate calculation. For example, volume-based meters require:

$$Q_{energy,\ volume-based} = Q_{v,std} H_{v,std} = \left(\frac{\rho Q_v}{\rho_{std}}\right)(\rho_{std} H_m) \qquad [1\text{-}1]$$

$$= Q_v(\rho H_m) = Q_v H_v$$

Thus, to complete the energy flow rate calculation, volume-based meters require only the volume-based heating value, $H_v$ [Btu/acf], which is the product of flowing density, $\rho$ [lbm/ft$^3$], and mass-based heating value, $H_m$ [Btu/lbm]. If traditional formulations of standard volumetric flow rate, $Q_{v,std}$ [scf/h], and heating value, $H_{v,std}$ [Btu/scf], are desired, then standard density, $\rho_{std}$ [typically measured in lbm/ft$^3$ at 60° F., 14.73 psia, at the flowing composition], is also needed.

Energy flow rate through a differential (pressure-based) meter requires:

$$Q_{energy,\ differential-based} = Q_{v,std} H_{v,std} = \left(\frac{C\sqrt{\rho}}{\rho_{std}}\right)(\rho_{std} H_m) \qquad [1\text{-}2]$$

$$= C(\sqrt{\rho}\ H_m)$$

Note that differential meters require determination of the flowing gas density, $\rho$[lbm/ft$^3$], and the mass-based heating value, $H_m$[Btu/lbm]. If traditional formulations of standard volumetric flow rate, $Q_{v,std}$ [scf/h], and heating value, $H_{v,std}$ [Btu/scf], are desired, then standard density, $\rho_{std}$ [typically lbm/ft$^3$ at 60° F., 14.73 psia, at the flowing composition], is also needed. Note that the catch-all factor C depends on the viscosity, $\mu$ (through the discharge coefficient), and on the isentropic exponent, $\kappa$ (through the expansion factor), but these are of lesser importance.

Energy flow rate calculation using a mass-based meter requires:

$$Q_{energy,\ mass-based} = Q_{v,std} H_{v,std} = \left(\frac{Q_m}{\rho_{std}}\right)(\rho_{std} H_m) = Q_m H_m \qquad [1\text{-}3]$$

Only the addition of mass-based heating value, $H_m$ [Btu/lbm], is required to determine energy flow rate through a mass-based meter. If traditional formulations of standard volumetric flow rate, $Q_{v,std}$ [scf/h], and heating value, $H_{v,std}$ [Btu/scf], are desired, then the standard density, $\rho_{std}$, will also be needed to convert from a mass-basis to a standard-volume basis.

Equations [1-1] to [1-3] describe the property dependence of different meter classes with respect to energy measurement, but all properties are not equally difficult to determine. Chemical properties depend only on gas composition (chemical characterization). Thermodynamic properties depend on gas composition, temperature, and pressure. Furthermore, thermodynamic properties can become chemical properties (dependent only on gas composition) at a fixed temperature and pressure, although the chemical dependence will vary at different temperature and pressure conditions.

Thus, three natural gas properties are critical to energy measurement. Two chemical properties, $H_m$ and $\rho_{std}$, are required by all three meter classes, and an additional thermodynamic property ($\rho$) is required by volume-based and differential-based meters. Mass-based meters are uniquely independent of thermodynamic properties, an important advantage that makes flowing gas temperature and pressure irrelevant for this class of meters.

Other chemical properties, in addition to $H_m$ and $\rho_{std}$, are also useful. Mixture Molecular Weight, M [lbm/lb-mol], is useful as a data correlation intermediary to characterize gas composition, and may also be used to calculate Ideal Specific Gravity. Mixture Molar Ideal Gross Heating Value, $H_{n,ref}$ [kJ/mol, with chemical-enthalpies referenced to 25° C., 0.101325 MPa], is a useful intermediary to characterizing gas composition, especially gas density, ρ, from an existing equation of state.

The basis of inferential property determination is chemical characterization. Chemical properties are constant across gas-phase temperature and pressure conditions. In contrast, thermodynamic properties must be chemically characterized for selected temperature and pressure conditions.

For the purpose of defining various chemical properties and deriving data correlations, a database of 102 different natural gas compositions was developed. Of the first 51 compositions, 43 are unique. The remaining 51 compositions can be obtained by reversing the carbon dioxide and nitrogen concentrations of the first 51 compositions. The complete gas composition database is presented in Table 1.

TABLE 1

| ID# | nitrogen [mole %] | carbon dioxide [mole %] | methane [mole %] | ethane [mole %] | propane [mole %] | i-butane [mole %] | n-butane [mole %] | i-pentane [mole %] | n-pentane [mole %] | n-hexane [mole %] | n-heptane [mole %] | n-octane [mole %] |
|---|---|---|---|---|---|---|---|---|---|---|---|---|
| 1 | 0.4422 | 1.9285 | 84.3361 | 8.8946 | 3.1919 | 0.59064 | 0.39376 | 0.10950 | 0.07300 | 0.0325 | 0.0061 | 0.0012 |
| 2 | 1.6004 | 0.2331 | 95.5340 | 1.8790 | 0.4926 | 0.09066 | 0.06044 | 0.03522 | 0.02348 | 0.0309 | 0.0168 | 0.0034 |
| 3 | 5.6769 | 1.4546 | 85.1473 | 5.4174 | 1.5968 | 0.30438 | 0.20292 | 0.08694 | 0.05796 | 0.0391 | 0.0138 | 0.0019 |
| 4 | 0.6224 | 1.8643 | 85.4814 | 8.0607 | 2.8624 | 0.52170 | 0.34780 | 0.11346 | 0.07564 | 0.0398 | 0.0096 | 0.0008 |
| 5 | 5.4939 | 1.8292 | 84.3931 | 5.8857 | 1.6910 | 0.32742 | 0.21828 | 0.06942 | 0.04628 | 0.0296 | 0.0128 | 0.0033 |
| 6 | 5.3551 | 1.7802 | 84.4786 | 5.8782 | 1.7778 | 0.34002 | 0.22668 | 0.07050 | 0.04700 | 0.0309 | 0.0116 | 0.0034 |
| 7 | 1.6052 | 0.2339 | 95.5192 | 1.8835 | 0.4933 | 0.09108 | 0.06072 | 0.03546 | 0.02364 | 0.0326 | 0.0176 | 0.0038 |
| 8 | 0.4278 | 1.8497 | 84.4678 | 8.8604 | 3.1831 | 0.58008 | 0.38672 | 0.11994 | 0.07996 | 0.0369 | 0.0068 | 0.0008 |
| 9 | 5.6760 | 1.4579 | 85.1666 | 5.4022 | 1.5922 | 0.30366 | 0.20244 | 0.08706 | 0.05804 | 0.0385 | 0.0134 | 0.0020 |
| 10 | 0.6122 | 1.8630 | 85.4915 | 8.0626 | 2.8576 | 0.52254 | 0.34836 | 0.11412 | 0.07608 | 0.0404 | 0.0100 | 0.0016 |
| 11 | 1.6052 | 0.2339 | 95.5192 | 1.8835 | 0.4933 | 0.09108 | 0.06072 | 0.03546 | 0.02364 | 0.0326 | 0.0176 | 0.0038 |
| 12 | 0.4278 | 1.8497 | 84.4678 | 8.8604 | 3.1831 | 0.58008 | 0.38672 | 0.11994 | 0.07996 | 0.0369 | 0.0068 | 0.0008 |
| 13 | 5.6760 | 1.4579 | 85.1666 | 5.4022 | 1.5922 | 0.30366 | 0.20244 | 0.08706 | 0.05804 | 0.0385 | 0.0134 | 0.0020 |
| 14 | 0.6122 | 1.8630 | 85.4915 | 8.0626 | 2.8576 | 0.52254 | 0.34836 | 0.11412 | 0.07608 | 0.0404 | 0.0100 | 0.0016 |
| 15 | 1.6032 | 0.2299 | 95.5480 | 1.8724 | 0.4883 | 0.08982 | 0.05988 | 0.03462 | 0.02308 | 0.0312 | 0.0164 | 0.0032 |
| 16 | 0.4293 | 1.8647 | 84.4333 | 8.8669 | 3.1897 | 0.58182 | 0.38788 | 0.12066 | 0.08044 | 0.0377 | 0.0072 | 0.0004 |
| 17 | 5.6680 | 1.4349 | 85.1784 | 5.4163 | 1.5962 | 0.30426 | 0.20284 | 0.08706 | 0.05804 | 0.0387 | 0.0131 | 0.0022 |
| 18 | 0.6137 | 1.8710 | 85.4620 | 8.0768 | 2.8634 | 0.52272 | 0.34848 | 0.11412 | 0.07608 | 0.0405 | 0.0101 | 0.0011 |
| 19 | 2.3535 | 0.0401 | 92.2794 | 3.7252 | 0.9170 | 0.26166 | 0.17444 | 0.08898 | 0.05932 | 0.0654 | 0.0115 | 0.0235 |
| 20 | 2.6733 | 0.0402 | 93.0357 | 3.1217 | 0.6420 | 0.16896 | 0.11264 | 0.06930 | 0.04620 | 0.0436 | 0.0229 | 0.0235 |
| 21 | 2.4630 | 1.5280 | 90.8251 | 4.4050 | 0.6420 | 0.06774 | 0.04516 | 0.01386 | 0.00924 | 0.0003 | 0.0006 | 0.0000 |
| 22 | 0.4040 | 1.9870 | 83.9520 | 9.1380 | 3.2590 | 0.59340 | 0.39560 | 0.12640 | 0.08360 | 0.0473 | 0.0139 | 0.0008 |
| 23 | 0.4050 | 2.0270 | 83.8681 | 9.1800 | 3.2790 | 0.58560 | 0.39040 | 0.12294 | 0.08196 | 0.0459 | 0.0136 | 0.0005 |
| 24 | 0.3940 | 1.9730 | 83.7500 | 9.3490 | 3.3080 | 0.58040 | 0.38720 | 0.11976 | 0.07984 | 0.0447 | 0.0133 | 0.0004 |
| 25 | 1.2630 | 1.9820 | 88.9650 | 5.4550 | 1.6160 | 0.30780 | 0.20520 | 0.09780 | 0.06520 | 0.0310 | 0.0120 | 0.0000 |
| 26 | 4.1950 | 1.5730 | 87.9810 | 4.8020 | 0.9080 | 0.18840 | 0.12560 | 0.09300 | 0.06200 | 0.0450 | 0.0260 | 0.0010 |
| 27 | 1.9080 | 1.9860 | 92.7220 | 2.7990 | 0.3430 | 0.06180 | 0.04120 | 0.06420 | 0.04280 | 0.0150 | 0.0170 | 0.0000 |
| 28 | 5.1240 | 0.5810 | 88.8020 | 4.1500 | 0.8580 | 0.17940 | 0.11960 | 0.07320 | 0.04880 | 0.0400 | 0.0220 | 0.0020 |
| 29 | 4.9480 | 1.6030 | 86.6460 | 4.9600 | 1.2440 | 0.24180 | 0.16120 | 0.08640 | 0.05760 | 0.0340 | 0.0170 | 0.0010 |
| 30 | 0.4230 | 2.1250 | 84.0050 | 8.7790 | 3.2380 | 0.64740 | 0.43160 | 0.16740 | 0.11160 | 0.0590 | 0.0130 | 0.0000 |
| 31 | 2.4750 | 1.7790 | 87.9700 | 5.5520 | 1.5120 | 0.29520 | 0.19680 | 0.09840 | 0.06560 | 0.0360 | 0.0190 | 0.0010 |
| 32 | 5.5400 | 1.7960 | 86.4450 | 4.7560 | 0.9140 | 0.19860 | 0.13240 | 0.08580 | 0.05720 | 0.0460 | 0.0260 | 0.0030 |
| 33 | 2.5050 | 0.9750 | 92.3210 | 3.2850 | 0.5690 | 0.11100 | 0.07400 | 0.06000 | 0.04000 | 0.0350 | 0.0230 | 0.0020 |
| 34 | 4.1230 | 0.7040 | 90.4400 | 3.5110 | 0.7500 | 0.17040 | 0.11360 | 0.07140 | 0.04760 | 0.0410 | 0.0250 | 0.0030 |
| 35 | 1.0370 | 2.0360 | 88.0480 | 6.2390 | 1.8390 | 0.36780 | 0.24520 | 0.09120 | 0.06080 | 0.0260 | 0.0080 | 0.0020 |
| 36 | 0.6122 | 1.8630 | 85.4915 | 8.0626 | 2.8576 | 0.52254 | 0.34836 | 0.11412 | 0.07608 | 0.0404 | 0.0100 | 0.0016 |
| 37 | 0.6137 | 1.8710 | 85.4620 | 8.0768 | 2.8634 | 0.52272 | 0.34848 | 0.11412 | 0.07608 | 0.0405 | 0.0101 | 0.0011 |
| 38 | 0.6178 | 1.9051 | 85.3453 | 8.1433 | 2.8692 | 0.53850 | 0.35900 | 0.10470 | 0.06980 | 0.0345 | 0.0117 | 0.0011 |
| 39 | 3.7924 | 0.2609 | 94.6077 | 1.0118 | 0.2128 | 0.04572 | 0.03048 | 0.01464 | 0.00976 | 0.0086 | 0.0044 | 0.0008 |
| 40 | 0.9015 | 0.0668 | 98.2722 | 0.5159 | 0.1607 | 0.03552 | 0.02368 | 0.00942 | 0.00628 | 0.0055 | 0.0016 | 0.0009 |
| 41 | 0.4313 | 1.7708 | 85.4560 | 8.4983 | 2.7421 | 0.53706 | 0.35804 | 0.10038 | 0.06692 | 0.0315 | 0.0068 | 0.0008 |
| 42 | 5.3551 | 1.7802 | 84.4784 | 5.8782 | 1.7780 | 0.34002 | 0.22668 | 0.07050 | 0.04700 | 0.0309 | 0.0116 | 0.0034 |
| 43 | 5.4939 | 1.8292 | 84.3931 | 5.8857 | 1.6910 | 0.32742 | 0.21828 | 0.06942 | 0.04628 | 0.0296 | 0.0128 | 0.0033 |
| 44 | 5.3452 | 1.7745 | 84.5143 | 5.8831 | 1.7596 | 0.33582 | 0.22388 | 0.07044 | 0.04696 | 0.0309 | 0.0119 | 0.0034 |
| 45 | 5.4952 | 1.8318 | 84.3746 | 5.8795 | 1.7111 | 0.32880 | 0.21920 | 0.06906 | 0.04604 | 0.0297 | 0.0117 | 0.0033 |
| 46 | 0.9617 | 1.5021 | 85.9284 | 8.4563 | 2.3022 | 0.41910 | 0.27940 | 0.07308 | 0.04872 | 0.0228 | 0.0057 | 0.0005 |
| 47 | 0.4284 | 1.9201 | 84.3789 | 8.8749 | 3.1776 | 0.60132 | 0.40088 | 0.10872 | 0.07248 | 0.0310 | 0.0065 | 0.0012 |
| 48 | 1.2010 | 1.8560 | 88.2210 | 6.1190 | 1.8840 | 0.35340 | 0.23560 | 0.05580 | 0.03720 | 0.0230 | 0.0130 | 0.0010 |
| 49 | 0.3407 | 1.8816 | 83.4187 | 9.5284 | 3.5694 | 0.62190 | 0.41460 | 0.10968 | 0.07312 | 0.0327 | 0.0081 | 0.0011 |
| 50 | 5.9990 | 1.3984 | 84.4872 | 5.9271 | 1.5364 | 0.30534 | 0.20356 | 0.06342 | 0.04228 | 0.0251 | 0.0101 | 0.0021 |
| 51 | 1.4200 | 0.0330 | 93.3240 | 1.7800 | 3.2000 | 0.08700 | 0.05800 | 0.02520 | 0.01680 | 0.0560 | 0.0000 | 0.0000 |
| 52 | 1.9285 | 0.4422 | 84.3361 | 8.8946 | 3.1919 | 0.59064 | 0.39376 | 0.10950 | 0.07300 | 0.0325 | 0.0061 | 0.0012 |
| 53 | 0.2331 | 1.6004 | 95.5340 | 1.8790 | 0.4926 | 0.09066 | 0.06044 | 0.03522 | 0.02348 | 0.0309 | 0.0168 | 0.0034 |
| 54 | 1.4546 | 5.6769 | 85.1473 | 5.4174 | 1.5968 | 0.30438 | 0.20292 | 0.08694 | 0.05796 | 0.0391 | 0.0138 | 0.0019 |
| 55 | 1.8643 | 0.6224 | 85.4814 | 8.0607 | 2.8624 | 0.52170 | 0.34780 | 0.11346 | 0.07564 | 0.0398 | 0.0096 | 0.0008 |
| 56 | 1.8292 | 5.4939 | 84.3931 | 5.8857 | 1.6910 | 0.32742 | 0.21828 | 0.06942 | 0.04628 | 0.0296 | 0.0128 | 0.0033 |
| 57 | 1.7802 | 5.3551 | 84.4786 | 5.8782 | 1.7778 | 0.34002 | 0.22668 | 0.07050 | 0.04700 | 0.0309 | 0.0116 | 0.0034 |
| 58 | 0.2339 | 1.6052 | 95.5192 | 1.8835 | 0.4933 | 0.09108 | 0.06072 | 0.03546 | 0.02364 | 0.0326 | 0.0176 | 0.0038 |
| 59 | 1.8497 | 0.4278 | 84.4678 | 8.8604 | 3.1831 | 0.58008 | 0.38672 | 0.11994 | 0.07996 | 0.0369 | 0.0068 | 0.0008 |
| 60 | 1.4579 | 5.6790 | 85.1666 | 5.4022 | 1.5922 | 0.30366 | 0.20244 | 0.08706 | 0.05804 | 0.0385 | 0.0134 | 0.0020 |
| 61 | 1.8630 | 0.6122 | 85.4915 | 8.0626 | 2.8576 | 0.52254 | 0.34836 | 0.11412 | 0.07608 | 0.0404 | 0.0100 | 0.0016 |
| 62 | 0.2339 | 1.6052 | 95.5192 | 1.8835 | 0.4933 | 0.09108 | 0.06072 | 0.03546 | 0.02364 | 0.0326 | 0.0176 | 0.0038 |
| 63 | 1.8497 | 0.4278 | 84.4578 | 8.8604 | 3.1831 | 0.58008 | 0.38672 | 0.11994 | 0.07996 | 0.0369 | 0.0068 | 0.0008 |

TABLE 1-continued

| ID# | nitrogen [mole %] | carbon dioxide [mole %] | methane [mole %] | ethane [mole %] | propane [mole %] | i-butane [mole %] | n-butane [mole %] | i-pentane [mole %] | n-pentane [mole %] | n-hexane [mole %] | n-heptane [mole %] | n-octane [mole %] |
|---|---|---|---|---|---|---|---|---|---|---|---|---|
| 64 | 1.4579 | 5.6760 | 85.1666 | 5.4022 | 1.5922 | 0.30366 | 0.20244 | 0.08706 | 0.05804 | 0.0385 | 0.0134 | 0.0020 |
| 65 | 1.8630 | 0.6122 | 85.4915 | 8.0626 | 2.8576 | 0.52254 | 0.34836 | 0.11412 | 0.07608 | 0.0404 | 0.0100 | 0.0016 |
| 66 | 0.2299 | 1.6032 | 95.5480 | 1.8724 | 0.4883 | 0.08982 | 0.05988 | 0.03482 | 0.02308 | 0.0312 | 0.0164 | 0.0032 |
| 67 | 1.8647 | 0.4293 | 84.4333 | 8.8669 | 3.1897 | 0.58182 | 0.38788 | 0.12066 | 0.08044 | 0.0377 | 0.0072 | 0.0004 |
| 68 | 1.4349 | 5.6680 | 85.1784 | 5.4163 | 1.5962 | 0.30426 | 0.20284 | 0.08706 | 0.05804 | 0.0387 | 0.0131 | 0.0022 |
| 69 | 1.8710 | 0.6137 | 85.4620 | 8.0768 | 2.8634 | 0.52272 | 0.34848 | 0.11412 | 0.07608 | 0.0405 | 0.0101 | 0.0011 |
| 70 | 0.0401 | 2.3535 | 92.2794 | 3.7252 | 0.9170 | 0.26166 | 0.17444 | 0.08898 | 0.05932 | 0.0654 | 0.0115 | 0.0235 |
| 71 | 0.0402 | 2.6733 | 93.0357 | 3.1217 | 0.6420 | 0.16896 | 0.11264 | 0.06930 | 0.04620 | 0.0436 | 0.0229 | 0.0235 |
| 72 | 1.5280 | 2.4630 | 90.8251 | 4.4050 | 0.6420 | 0.06774 | 0.04516 | 0.01386 | 0.00924 | 0.0003 | 0.0006 | 0.0000 |
| 73 | 1.9870 | 0.4040 | 83.9520 | 9.1380 | 3.2590 | 0.59340 | 0.39560 | 0.12540 | 0.08360 | 0.0473 | 0.0139 | 0.0008 |
| 74 | 2.0270 | 0.4050 | 83.8681 | 9.1800 | 3.2790 | 0.58560 | 0.39040 | 0.12294 | 0.08196 | 0.0459 | 0.0136 | 0.0005 |
| 75 | 1.9730 | 0.3940 | 83.7500 | 9.3490 | 3.3080 | 0.58080 | 0.38720 | 0.11976 | 0.07984 | 0.0447 | 0.0133 | 0.0004 |
| 76 | 1.9820 | 1.2630 | 88.9650 | 5.4550 | 1.6160 | 0.30780 | 0.20520 | 0.09780 | 0.06520 | 0.0310 | 0.0120 | 0.0000 |
| 77 | 1.5730 | 4.1950 | 87.9810 | 4.8020 | 0.9080 | 0.18840 | 0.12560 | 0.09300 | 0.06200 | 0.0450 | 0.0260 | 0.0010 |
| 78 | 1.9860 | 1.9080 | 92.7220 | 2.7990 | 0.3430 | 0.06180 | 0.04120 | 0.06420 | 0.04280 | 0.0150 | 0.0170 | 0.0000 |
| 79 | 0.5810 | 5.1240 | 88.8020 | 4.1500 | 0.8580 | 0.17940 | 0.11960 | 0.07320 | 0.04880 | 0.0400 | 0.0220 | 0.0020 |
| 80 | 1.6030 | 4.9480 | 86.6460 | 4.9600 | 1.2440 | 0.24180 | 0.16120 | 0.08640 | 0.05760 | 0.0340 | 0.0170 | 0.0010 |
| 81 | 2.1250 | 0.4230 | 84.0050 | 8.7790 | 3.2380 | 0.64740 | 0.43160 | 0.16740 | 0.11160 | 0.0590 | 0.0130 | 0.0000 |
| 82 | 1.7790 | 2.4750 | 87.9700 | 5.5520 | 1.5120 | 0.29520 | 0.19680 | 0.09840 | 0.06560 | 0.0360 | 0.0190 | 0.0010 |
| 83 | 1.7960 | 5.5400 | 86.4450 | 4.7560 | 0.9140 | 0.19860 | 0.13240 | 0.08580 | 0.05720 | 0.0460 | 0.0260 | 0.0030 |
| 84 | 0.9750 | 2.5050 | 92.3210 | 3.2850 | 0.5690 | 0.11100 | 0.07400 | 0.06000 | 0.04000 | 0.0350 | 0.0230 | 0.0020 |
| 85 | 0.7040 | 4.1230 | 90.4400 | 3.5110 | 0.7500 | 0.17048 | 0.11360 | 0.07140 | 0.04760 | 0.0410 | 0.0250 | 0.0030 |
| 86 | 2.0360 | 1.0370 | 88.0480 | 6.2390 | 1.8390 | 0.36780 | 0.24520 | 0.09120 | 0.06080 | 0.0260 | 0.0080 | 0.0020 |
| 87 | 1.8630 | 0.6122 | 85.4915 | 8.0626 | 2.8576 | 0.52254 | 0.34836 | 0.11412 | 0.07608 | 0.0404 | 0.0100 | 0.0016 |
| 88 | 1.8710 | 0.6137 | 85.4620 | 8.0768 | 2.8634 | 0.52272 | 0.34848 | 0.11412 | 0.07608 | 0.0405 | 0.0101 | 0.0011 |
| 89 | 1.9051 | 0.6178 | 85.3453 | 8.1433 | 2.8692 | 0.53850 | 0.35900 | 0.10470 | 0.06980 | 0.0345 | 0.0117 | 0.0011 |
| 90 | 0.2609 | 3.7924 | 94.6077 | 1.0118 | 0.2128 | 0.04572 | 0.03048 | 0.01464 | 0.00976 | 0.0086 | 0.0044 | 0.0008 |
| 91 | 0.0668 | 0.9015 | 98.2722 | 0.5159 | 0.1607 | 0.03552 | 0.02368 | 0.00942 | 0.00628 | 0.0055 | 0.0016 | 0.0009 |
| 92 | 1.7708 | 0.4313 | 85.4560 | 8.4983 | 2.7421 | 0.53706 | 0.35804 | 0.10038 | 0.06692 | 0.0315 | 0.0068 | 0.0008 |
| 93 | 1.7802 | 5.3551 | 84.4784 | 5.8782 | 1.7780 | 0.34002 | 0.22668 | 0.07050 | 0.04700 | 0.0309 | 0.0116 | 0.0034 |
| 94 | 1.8292 | 5.4939 | 84.3931 | 5.8857 | 1.6910 | 0.32742 | 0.21828 | 0.06942 | 0.04628 | 0.0296 | 0.0128 | 0.0033 |
| 95 | 1.7745 | 5.3452 | 84.5143 | 5.8831 | 1.7596 | 0.33582 | 0.22388 | 0.07044 | 0.04696 | 0.0309 | 0.0119 | 0.0034 |
| 96 | 1.8318 | 5.4952 | 84.3746 | 5.8795 | 1.7111 | 0.32880 | 0.21920 | 0.06906 | 0.04604 | 0.0297 | 0.0117 | 0.0033 |
| 97 | 1.5021 | 0.9617 | 85.9284 | 8.4563 | 2.3022 | 0.41910 | 0.27940 | 0.07308 | 0.04872 | 0.0228 | 0.0057 | 0.0005 |
| 98 | 1.9201 | 0.4264 | 84.3789 | 8.8749 | 3.1776 | 0.60132 | 0.40088 | 0.10872 | 0.07248 | 0.0310 | 0.0065 | 0.0012 |
| 99 | 1.8560 | 1.2010 | 88.1210 | 6.1190 | 1.8840 | 0.35340 | 0.23560 | 0.05580 | 0.03720 | 0.0230 | 0.0130 | 0.0010 |
| 100 | 1.8816 | 0.3407 | 83.4187 | 9.5264 | 3.5694 | 0.62190 | 0.41460 | 0.10968 | 0.07312 | 0.0327 | 0.0081 | 0.0011 |
| 101 | 1.3984 | 5.9990 | 84.4872 | 5.9271 | 1.5364 | 0.30534 | 0.20356 | 0.06342 | 0.04228 | 0.0251 | 0.0101 | 0.0021 |
| 102 | 0.0330 | 1.4200 | 93.3240 | 1.7800 | 3.2000 | 0.08700 | 0.05800 | 0.02520 | 0.01680 | 0.0560 | 0.0000 | 0.0000 |

The values for M, $H_m$, $\rho_{std}$, and $H_{n,ref}$ can be calculated using the model equations shown below, and the composition values from Table 1 for each natural gas composition.

$$M = \sum_{i=1}^{N} \left( \frac{X_i}{100} M_i \right) \quad [1\text{-}4]$$

where N is the number of pure gas components in the mixture, $X_i$ is the mole percentage of each component, and $M_i$ is the molecular weight of each component (from the Gas Processor's Association (GPA) Standard 2145 (1994)).

$$H_m = \frac{\sum_{i=1}^{N} \left( \frac{X_i}{100} M_i H_{m,i} \right)}{M} \quad [1\text{-}5]$$

where N is the number of pure gas components in the mixture, $X_i$ is the mole percentage of each component, $M_i$ is the molecular weight of each component, and $H_{m,i}$ is the mass-based heating value of each component (from the GPA) Standard 2145 (1994). In the natural gas industry, it is standard practice to use chemical enthalpies (heating values) determined at standard conditions of 60° F. and 14.696 psia, even though the volumetric basis is often converted to a pressure of 14.73 psia. The GPA Standard 2145 (1994) provides the $H_{m,i}$ data at the accepted chemical enthalpy conditions of 60° F. and 14.696 psia.

$$\rho_{std} = \frac{P_{std} M}{Z R T_{std}} \quad [1\text{-}6]$$

In this case, the real gas state equation is used, where $P_{std}$ and $T_{std}$ are standard pressure and temperature (absolute units), M is the mixture molecular weight, Z is the compressibility factor, and R is the universal gas constant. Since $P_{std}$, $T_{std}$, and R are all constants, $\rho_{std}$ is a function of only the variable ratio M/Z.

$$H_{n,ref} = \sum_{i=1}^{N} \left( \frac{X_i}{100} H_{n,ref,i} \right) \quad [1\text{-}7]$$

where $X_i$ is the mole percentage of each pure gas component, and $H_{n,ref,i}$ is the molar ideal gross heating value (at 25° C. and 0.101325 MPa) of each pure gas component (from American Gas Association (A.G.A) Transmission Committee Report 8 (1994)).

Assuming three inferential gas characterization properties are known, namely, the speed of sound at 60° F. and 14.73 psia, $S_{std}$ [ft/s], the carbon dioxide concentration, $X_{CO2}$ [mol %], and the nitrogen concentration, $X_{N2}$ [mol %], and that the Mixture Molecular Weight, M, has a quadratic relationship with respect to the standard sound speed, $S_{std}$, such that the $S_{std}$ can be calculated using the commercially available SonicWare™ software or the GRI Extended Thermodynamic Properties Computer Programs (Gas Research Institute 1989, unpublished) at 60° F. and 14.73 psia, the form of the inferential correlation may be chosen as:

$$M = A + BS_{std} + CS_{std}^2 \quad [1\text{-}8]$$

where: $A = A_0 + A_1 X_{N2} + A_2 X_{CO2}$, $B = B_0 + B_1 X_{N2} + B_2 X_{CO2}$, and $C = C_0 + C_1 X_{N2} + C_2 X_{CO2}$.

A least squares curve fit of the data in Table 1 produces the following values for the unknown constants: $A_0 = 89.59987$, $A_1 = 0.2595616$, $A_2 = 0.8420112$, $B_0 = -0.08303539$, $B_1 = -3.57614 \, e^{-4}$, $B_2 = -1.20199 \, e^{-3}$, $C_0 = 2.22787 \, e^{-5}$, $C_1 = 1.37342 \, e^{-7}$, and $C_2 = 4.51462 \, e^{-7}$.

Assuming knowledge of the same inferential gas characterization properties, that $H_{m,CO2} = H_{m,N2} = 0$ (i.e., that diluent gases have no heating value), and that $H_m$ is a weak function of hydrocarbon composition, the Hydrocarbon Molecular Weight, $M_{HC}$, may be defined as:

$$M_{HC} = M - \left(\frac{X_{CO2}}{100} M_{CO2}\right) - \left(\frac{X_{N2}}{100} M_{N2}\right) \quad [1\text{-}9]$$

A the form of the inferential correlation may be chosen as:

$$H_m = \left(\frac{A + BM_{HC}}{M}\right) \quad [1\text{-}10]$$

where: $B = B_0 + B_1 S_{std}$ and $B_1 = B_2 + B_3 X_{N2} + B_4 X_{CO2}$. A least squares curve fit of the data in Table 1 produces values for the unknown constants: $A = 54,343.048$, $B_0 = 20,442.406$, $B_2 = 0.04552871$, $B_3 = -0.02523803$, and $B_4 = -0.02568212$.

Even though gas density is, in general, a thermodynamic property, the standard density is a chemical property because it is evaluated at specific conditions of 60° F., 14.73 psia, and at the flowing gas composition.

Because M has already been correlated to inferential properties (See equation [1-8]), and Z varies only about 0.1% across the Table 1 database compositions due to the low-pressure standard condition, the form of the standard density correlation is straightforward. Therefore, the same correlation form as equation [1-8] may be used to determine unique correlation constants for standard density:

$$\rho_{std} = A + BS_{std} + CS_{std}^2 \quad [1\text{-}11]$$

where: $A = A_0 + A_1 X_{N2} + A_2 X_{CO2}$, $B = B_0 + B_1 X_{N2} + B_2 X_{CO2}$, and $C = C_0 + C_1 X_{N2} + C_2 X_{CO2}$.

A least squares fit to the database of Table 1 produced values for the unknown constants: $A_0 = 0.2395147$, $A_1 = 7.067074 \, e^{-4}$, $A_2 = 2.334917 \, e^{-3}$, $B_0 = -2.228333 \, e^{-4}$, $B_1 = -9.87042 \, e^{-7}$, $B_2 = -3.35135 \, e^{-6}$, $C_0 = 5.99480 \, e^{-8}$, $C_1 = 3.81330 \, e^{-10}$, and $C_2 = 1.26106 \, e^{-9}$.

The Molar Ideal Gross Heating Value, at 25° C. and 0.101325 MPa reference conditions, is important as an intermediate variable that may be used to characterize natural gas composition for density calculations.

The form of the data correlation to inferential variables is chosen to be the same as that for the mass-based heating value, $H_m$, which is also a molar ideal gross heating value at a different reference state, using different units:

$$H_{n,ref} = A + BM_{HC} \quad [1\text{-}12]$$

where: $B = B_0 + B_1 S_{std}$, and $B_1 = B_2 + B_3 X_{N2} + B_4 X_{CO2}$. A least squares curve fit of the data in the Table 1 database produces values for the unknown constants: $A = 123.81271$, $B_0 = 47.41274$, $B_2 = 2.73661 \, e^{-4}$, $B_3 = -5.71187 \, e^{-5}$, $B_4 = -5.73574 \, e^{-5}$.

Thermodynamic properties are more difficult to characterize than chemical properties because chemical property dependence must be modeled as a function of temperature and pressure. As discussed with respect to various flow meters, gas density, $\rho$, is the most important thermodynamic property related to natural gas energy flow measurement. The Isentropic exponent, $\kappa$, and viscosity, $\mu$, are required for differential-based meters, but are less important because they form a part of less sensitive terms (the isentropic exponent is needed for the expansion factor, and viscosity is needed for the Reynolds number). Thus, it is important to be able to correlate gas density, $\rho$, to the pre-selected inferential properties of standard sound speed, $S_{std}$, carbon dioxide concentration, $X_{CO2}$, nitrogen concentration, $X_{N2}$, and, as noted above, the temperature, T, and pressure, P.

The U.S. natural gas industry currently has two well-accepted equations of state for computing natural gas density (i.e., the compressibility factor). These are contained in the A.G.A. Transmission Measurement Committee Report 8 (1994), referenced and included as if set forth entirely herein, and denominated as: the Detailed Characterization Method, which requires a detailed gas composition assay to characterize the gas, and the Gross Characterization Method, which requires inferential properties to characterize the gas. Both methods specify an uncertainty level of 0.1% over 32–130° F., up to 1200 psia, and gas compositions in the "normal range" detailed in Table 2.

TABLE 2

| Quantity | Normal Range |
|---|---|
| Relative Density* | 0.554–0.87 |
| Gross Heating Value**[Btu/scf] | 447–1,150 |
| Gross Heating Value***[MJ/m$^3$] | 18.7–45.1 |
| Methane [mol %] | 45.0–100.0 |
| Nitrogen [mol %] | 0–50.0 |
| Carbon Dioxide [mol %] | 0–30.0 |
| Ethane [mol %] | 0–10.0 |
| Propane [mol %] | 0–4.0 |
| Total Butanes [mol %] | 0–1.0 |
| Total Pentanes [mol %] | 0–0.3 |
| Hexanes Plus [mol %] | 0–0.2 |
| Helium [mol %] | 0–0.2 |
| Hydrogen [mol %] | 0–10.0 |
| Carbon Monoxide [mol %] | 0–3.0 |
| Water [mol %] | 0–0.05 |
| Hydrogen Sulfide [mol %] | 0–0.02 |

*Reference Condition: Relative density at 60° F., 14.73 psia
**Reference Conditions: Combustion at 60° F., 14.73 psia; density at 60° F., 14.73 psia.
***Reference Conditions: Combustion at 25° C., 0.101325 MPa; density at 0° C., 0.101325 MPa.

The current Gross Characterization Method allows the user to characterize a gas using one of two inferential variable sets: volumetric gross heating value, relative density, and carbon dioxide concentration (Method 1); or relative density, carbon dioxide concentration, and nitrogen concentration (Method 2). This invention introduces a new variable set: standard sound speed, $S_{std}$, carbon dioxide concentration, $X_{CO2}$, and nitrogen concentration, $X_{N2}$ (designated hereinafter as "Method 3").

The Gross Characterization Method is a virial equation of state, and is cast in terms of compressibility factor, Z, as a truncated expansion of molar density, d:

$$Z(T, P, \text{composition}) = \frac{\rho_{ideal\,gas}}{\rho_{real\,gas}} = 1 + B_{mix} d + C_{mix} d^2 \quad [1\text{-}13]$$

where compressibility factor, Z, is a dimensionless density, d is the molar density (a function of T, P, and composition), and the virial coefficients, $B_{mix}$ and $C_{mix}$, are complicated functions of temperature and composition. Since Z and d are both functions of temperature, T, pressure, P, and composition, the solution of Equation [1-13] is iterative.

The Gross Characterization method determines the virial coefficients, $B_{mix}$ and $C_{mix}$ by modeling the natural gas as a three component mixture containing carbon dioxide, nitrogen, and an equivalent hydrocarbon component. The equivalent hydrocarbon component is then characterized by one of the two inferential variable sets, using them to determine a single hydrocarbon characterization parameter, $H_{CH}$, which is the molar ideal gross heating value of the equivalent hydrocarbon [kJ/mol at reference conditions of 25° C. and 0.101325 MPa]. $H_{CH}$ is related to $H_{n,ref}$ by the following equation:

$$H_{CH} = \frac{H_{n,ref}}{\left(1 - \left(\frac{X_{CO2} + X_{N2}}{100}\right)\right)} \quad [1\text{-}14]$$

Since $H_{n,ref}$ has already been correlated to $S_{std}$, $X_{CO2}$, and $X_{N2}$ in Equation [1-12], $H_{CH}$ is now known as a function of the pre-selected inferential variables $S_{std}$, $X_{CO2}$, and $X_{N2}$, and can be used to characterize the equivalent hydrocarbon group for Method 3 of the Gross Characterization Method.

The most accurate way to determine $H_{CH}$ is from the detailed gas composition assay using Equations [1-7] and [1-14], but doing so defeats the purpose of gross inferential characterization. However, it is useful as a mechanism to verify the validity of the inferential characterization approach (i.e., Method 3) using the database of natural gas compositions in Table 1. Calculating natural gas density using both approaches over the entire temperature and pressure range of the A.G.A. Gross Characterization Method of Committee Report 8 provides two sets of residuals which agree within about ±0.05%.

As noted above, the speed of sound and component concentrations in the gas 30 may be determined directly, by measurement, or indirectly. For example, the concentration of nitrogen present within a natural gas mixture is difficult to measure directly. This is because nitrogen has low infrared absorption characteristics, and is chemically inert. However, there are indirect methods to determine the concentration of nitrogen within natural gas.

One Approach is to correlate the isentropic exponent, $\kappa_{std}$, at standard temperature (60° F.) and standard pressure (14.73 psia) to the inferential variables, $X_{CO2}$, $X_{N2}$ and $S_{std}$. For an ideal gas, the isentropic exponent is the same as the ratio of the constant pressure to the constant volume specific heats, $\kappa = c_p/c_v$, where $c_p$ and $C_v$ are molar specific heats, measured in units of Btu/lbmole-° F. The ideal gas assumption is reasonable in regions of low pressure and high temperature, well away from the dew point for a natural gas mixture.

Using readily-available computer programs well known in the art to calculate values of $c_p$, $c_v$ and sound speed $S_{std}$ for various distinct natural gas compositions at standard temperature and pressure, $\kappa_{std}$ values can be calculated as the ratio of the two specific heats. Such calculations show that $\kappa_{std}$ varies in an approximately linear manner as a function of standard sound speed, and increases in accord with the diluent concentration. Thus, a correlation may be developed for the ratio of specific heats (i.e. $\kappa_{std}$) in terms of the standard sound speed $S_{std}$, the nitrogen concentration $X_{N2}$, and the carbon dioxide concentration $X_{CO2}$. Then, by measuring the ratio of specific heats experimentally, and knowing the experimental values of the standard sound speed and the carbon dioxide concentration, the value of the nitrogen concentration can be calculated.

A second approach involves heating a confined sample of the gas and inferring the value of $X_{N2}$ by measuring the temperature rise (and other properties) of the experiment. For a container with a gas mixture at standard temperature and pressure, the mass of the gas mixture inside the container is $m=V^*\rho_{STD}$, where V is the container volume in units of $ft^3$, and $\rho_{STD}$ is the gas mixture density in units of $lbm/ft^3$. If the gas is heated using an electrical heater to raise the temperature by an amount $\Delta T$, the amount of energy used to heat the gas can be measured as the product of the voltage across the heater times the current through the heater times the duration of heating in seconds. The gas in the container is heated at constant volume, such that the gas pressure rises slightly as a result of the temperature rise. The gas density within the container does not change because neither the container volume nor the mass of the gas changes. The amount of heat energy, $Q=\rho_{STD}*V*(c_v/MW)*\Delta T$.

If we measure Q and $\Delta T$, then $(\rho_{STD}*c_v/MW)=Q/(V*\Delta T)$ where V is known. The product of $(\rho_{STD}*c_v/MW)$ is a function of standard sound speed and diluent concentration, wherein the variation of the product $(\rho_{STD}*c_v/MW)$ can be modeled as a function of the standard sound speed and the diluent concentrations such that the parameters can be determined by regression analysis. Thus:

$(\rho_{STD}*c_v/MW)=A+B/S_{STD}+C/S_{STD}^2$ where $A=A_0+A_1*X_{N2}+A_2*X_{CO2}$ $B=B_0+B_1*X_{N2}+B_2*X_{CO2}$ $C=C_0+C_1*X_{N2}+C_2*X_{CO2}$ Using regression fitting to calculate values for the nine regression parameters.

| | | |
|---|---|---|
| $A_0 = 0.00248359$ | $A_1 = 0.000475082$ | $A_2 = 0.000653587$ |
| $B_0 = 11.0257$ | $B_2 = -1.67547$ | $B_2 = -2.3125$ |
| $C_0 = 14707.8$ | $C_1 = 1185.97$ | $C_2 = 1598$ |

The regression model can now be rearranged to predict the value of nitrogen concentration $X_{N2}$ given values for the standard sound speed $S_{STD}$ and the concentration of carbon dioxide $X_{CO2}$. Thus:

$X_{N2}=[(Q/V^*\Delta T)-(A_0+B_0/S_{std}+C_0/S_{std}^2)-X_{CO2}*(A_2+B_2/S_{std}+C_2/S_{std}^2)]/(A_1+B_1/S_{std}+C_1/S_{std}^2)$ This equation can be used to determine nitrogen concentration from measurements of the amount of energy transferred as heat to the gas mixture, the volume of the container, the temperature rise of the gas mixture before and after heating, the standard sound speed, and the concentration of carbon dioxide.

Actual values of the product $(\rho_{STD}*c_v/MW)$, actual values of standard sound speed, and actual values of carbon dioxide concentration were used to calculate values of nitrogen concentration using the inferential equation given above for the 86 distinct gas mixtures in Table 1. The calculated values of nitrogen concentration are compared to the actual value of nitrogen concentration for each gas mixture. The agreement between the calculated and the actual values is typically within 0.02%.

A third approach to determine the $N_2$ concentration is to measure the temperature rise of the gas as it flows through a chamber at a constant volumetric flow rate while thermal energy is added by an electrical heater. The gas flows through the chamber with a constant mass flow rate m'=ρ*V' where ρ is the gas density and V' is the volumetric flow rate. The rate of heat transfer from the electrical heating element to the gas, Q, is equal to the product of the voltage across the heater times the current through the heater. In steady state and with a steady flow of gas through the chamber, the thermal energy generated by the heating element is taken up by the gas stream and causes the temperature to rise by an amount equal to ΔT. Therefore, with steady flow, and in steady state (when thermal equilibrium has been reached), the rate of heat transfer to the gas stream is $$Q=\rho^* V'^*(c_p/MW)^* \Delta T$$

If we measure Q and ΔT, and the mass flow rate, m'=ρ*V' is held constant by a metering pump, then the quantity $c_p$/MW is a function of the standard sound speed and the diluent concentration. The same type of analytical model can be used to represent the quantity($c_p$/MW) as was used to represent ($\rho_{std}*c_v$/MW), although the values of the constants calculated by regression will change. Then an equation can be written and solved for the nitrogen concentration as:

$$X_{N2}=[(Q/m'^*\Delta T)-(A_0+B_0/S_{std}+C_0/S_{std}^2)-X_{CO2}^*(A_2+B_2/S_{std}+C_2/S_{std}^2)]/(A_1+B_1/S_{std}+C_1/S_{std}^2)$$

A fourth method for determining nitrogen concentration can be developed from another correlation for molecular weight, similar to that shown in equation [1-4], but generalized to use the sound speed measured at arbitrary values of temperature and pressure.

For example, the molecular weight of a natural gas mixture of unknown composition may be represented by an equation such as $$MW=(A_1+B_1/S_1+C_1/S_1^2)^*(1+D_1^*X_{N2}+E_1^*X_{CO2}) \quad [1\text{-}15]$$

The constants, $A_1$, $B_1$, $C_1$, $D_1$ and $E_1$ are functions of the gas temperature, $T_1$, and gas pressure $P_1$, but they are not functions of the gas composition. $S_1$ is the sound speed measured for the gas mixture at $T_1$ and $P_1$. At a second temperature, $T_2$, and pressure, P2, the equation becomes, $$MW=(A_2+B_2/S_2+C_2/S_2^2)^*(1+D_2^*X_{N2}+E_2^*X_{CO2}) \quad [1\text{-}16]$$

Using a readily available equation of state for natural gas mixtures, the values of the constants $A_1$ through $E_1$ and $A_2$ through $E_2$ can be calculated for two different values of gas temperature and/or pressure. One condition can be standard pressure and standard temperature. The $CO_2$ concentration must then be measured for the gas mixture under consideration. If values of the sound speed, $S_1$ and S2 are measured at the two pressure and temperature conditions, equations (1-15) and 1-16) can then be solved to give the nitrogen concentration as:

the speed of sound in gas may be determined by direct measurement, using an ultrasonic flow meter or transit-time measurement.

Once the speed of sound in the gas is determined, it is necessary to determine a plurality (two or more) of concentrations for various non-combustible components which comprise the gas in step 130. Examples using the concentrations of carbon dioxide and nitrogen concentration have been explicitly detailed. The thermophysical property determination via correlation in step 140 is then effected by an empirical process, as discussed in detail above.

The inferential correlation for various chemical properties may then be determined, including mixture molecular weight (M) in step 170, mass-based heating value ($H_m$) in step 180, standard density ($\rho_{STD}$) in step 190, mixture molar ideal gross heating value ($H_{n,ref}$) in step 200. Other properties may also be determined, such as molar specific heat at constant volume ($c_v$), molar specific heat at constant pressure ($c_p$), and the ratio of specific heats $\kappa=c_p/c_v$.

As has been noted, the standard heating value ($H_{v,std}$) can be calculated from the mass-based heating value, $H_m$, and the standard density, $\rho_{STD}$. This is accomplished in step 220. If the flow rate is determined in step 230, then the energy flow rate, which is the product of the standard heating value ($H_{v,std}$) and the flow rate ($Q_{std}$), can be determined in step 240, as shown above.

In summary, the method for determining thermophysical properties of a multi-component gas described above is based upon measuring the speed of sound in the natural gas mixture at standard pressure (14.73 psia) and standard temperature (60° F.), along with the molar concentrations of nitrogen, $X_{N2}$, and carbon dioxide, $X_{CO2}$. Since the speed of sound at standard pressure and temperature is related to the relative density of the natural gas mixture (the ratio of the natural gas mixture density to the air density) at standard pressure and temperature, it can be used in place of the relative density in the Gross Characterization Method of the A.G.A. Report no. 8 equation of state (designated as Method 3 above) to calculate the density and properties of the gas at flowing temperature and pressure.

It should be noted that an alternative approach to measuring the speed of sound at standard pressure and temperature has also been discovered, and provides the capability to develop an energy meter module compatible with conventional ultrasonic flow meters, which measure the speed of sound in flowing gas at pipeline pressure and temperature. This enables energy measurement at flowing pressure and temperature using only the pressure, temperature, and the molar concentrations of nitrogen and carbon dioxide.

Figure 3:
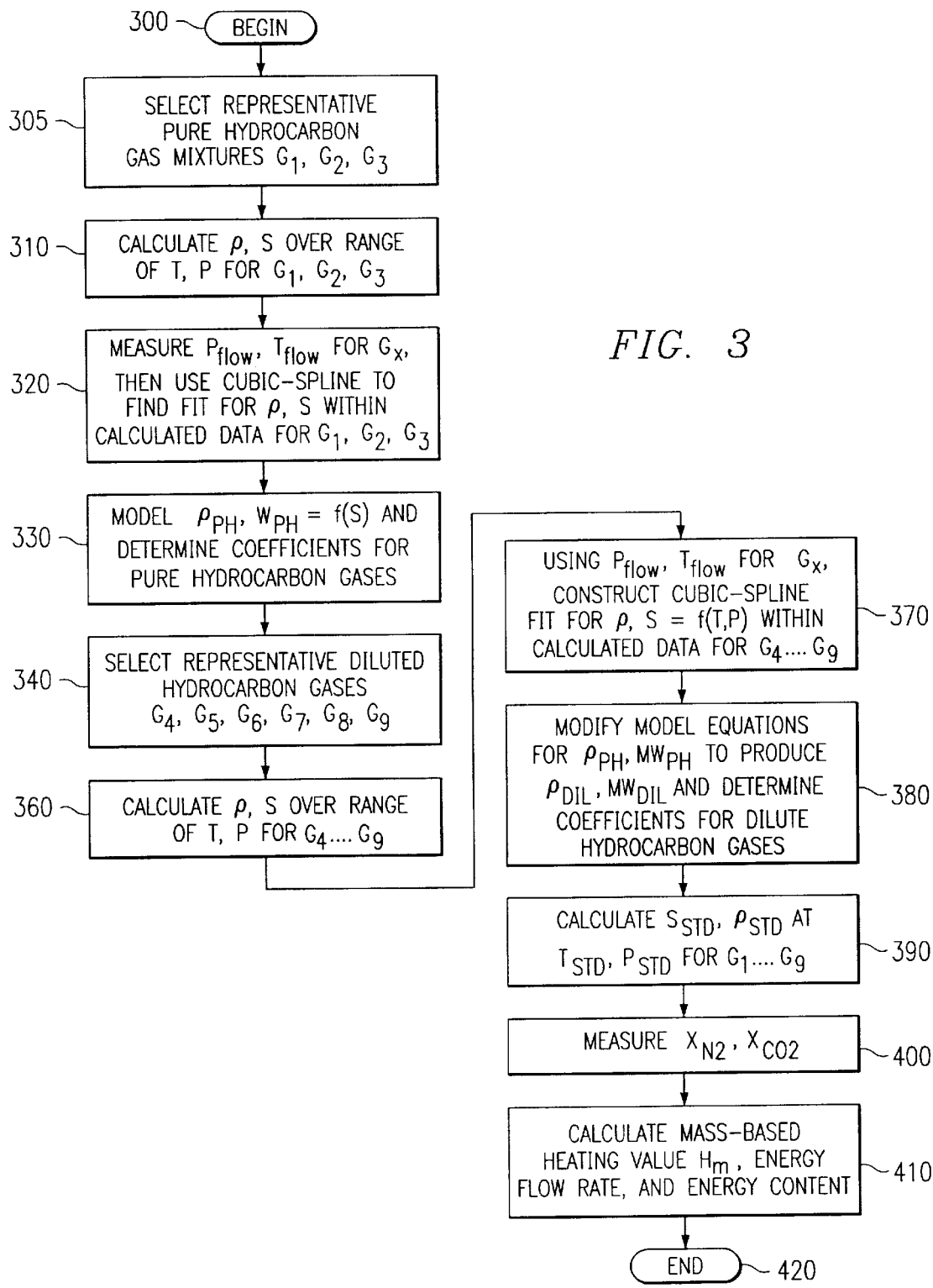
FIG. 3 is a flow diagram illustrating an alternative embodiment of the method of the present invention.

The method of the alternative approach is shown in FIG. 3, and begins at step 300, and in step 305 three natural gas mixture compositions $G_1$, G2, and $G_3$ are selected that cover the range of interest in natural gas molecular weight (MW). Each selected gas mixture comprises hydrocarbon gases only, which means that the diluent concentrations are 0.0

$$X_{N2} = \frac{\left(A_2+\frac{B_2}{S_2}+\frac{C_2}{S_2^2}\right)*(1+E_2*X_{CO2})-\left(A_1+\frac{B_1}{S_1}+\frac{C_1}{S_1^2}\right)*(1+E_1*X_{CO2})}{\left(A_1+\frac{B_1}{S_1}+\frac{C_1}{S_1^2}\right)*D_1-\left(A_2+\frac{B_2}{S_2}+\frac{C_2}{S_2^2}\right)*D_2} \quad [1\text{-}17]$$

Figure 2:
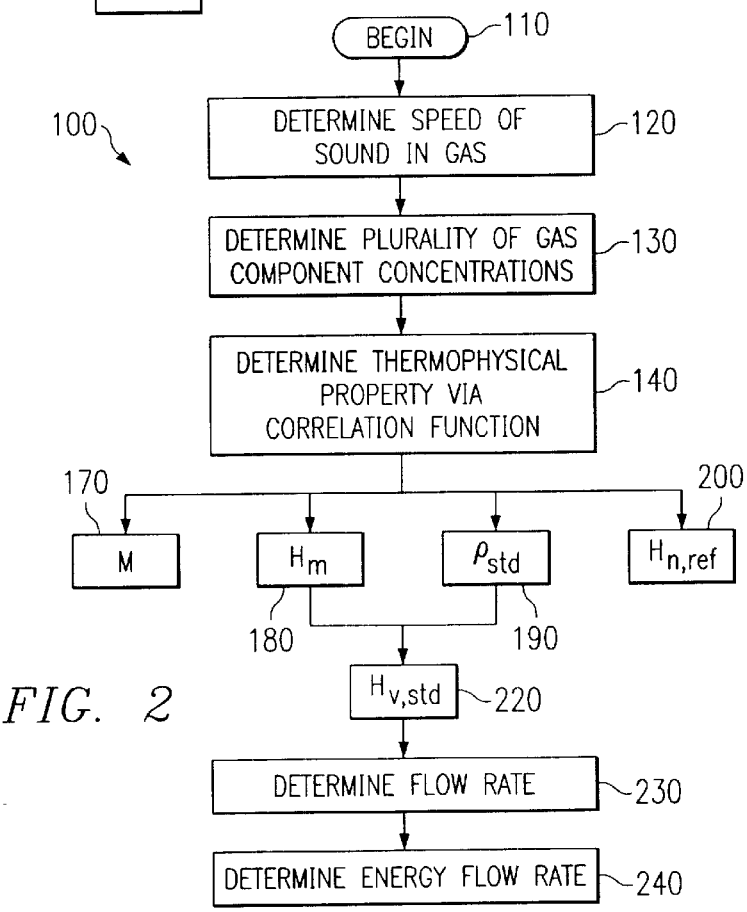
FIG. 2 is a flow diagram illustrating the method of determining thermophysical properties of a gas according to the present invention.

Turning now to FIG. 2, a flow chart diagram summarizing the method 100 of the present invention can be seen. The method begins at step 110 with determining the speed of sound in a multi-component gas in step 120. As noted above, mole % carbon dioxide and 0.0 mole % nitrogen. The selected pure hydrocarbon gas mixtures are similar to those identified in Table 1 as ID#40, 26, and 49. However, each of the selected gases has no nitrogen or carbon dioxide components, and therefore, the selected pure hydrocarbon gas mixtures will be identified as Gas ID#40_00_00=$G_1$ (for gas mixture ID# 40, that has no carbon dioxide, and no nitrogen), Gas ID#26_00_00=$G_2$, and Gas ID#49_00_00=$G_3$, respectively The digits_00_00 after the Gas ID# simply indicate that the mole % concentrations of carbon dioxide and nitrogen are equal to zero. Using standard calculations well known in the art, the selected gas mixtures $GI_1$, $G_2$, and $G_3$ are found to have molecular weights of MW1=16.202, MW2=17.318 and MW3=19.017 respectively.

In step 310, an existing commercial computer code (similar or identical to SonicWare™ software) is used to calculate values of the gas mixture density, $\rho$, and the speed of sound, S, for a matrix of values of gas temperature, T, and gas pressure, P for $G_1$, $G_2$, and $G_3$. For example, the temperature values may range from about 20° F. to about 150° F. in steps of 10° F., and the pressure values may include 14.73 psia, 50 psia, 100 psia, and a range of steps from 100 psia to 1400 psia, in steps of 100 psia. The calculated values of $\rho$, S, T and P may then be stored into three data files in the processor 80 memory, such as PROPS1.DAT, PROPS2.DAT and PROPS3.DAT.

At this point, the pressure and temperature of the natural gas mixture (whose composition is still unknown) flowing in the pipeline is measured and recorded as $P_{flow}$ and $T_{flow}$. The properties of the three gas mixtures $G_1$, G2, and G3 recorded in the files PROPS1.DAT, PROPS2.DAT and PROPS3.DAT are used with a cubic-spline fit algorithm to provide numerical (approximate) fits for density and the speed of sound as a function of temperature and pressure, using the measured values $P_{flow}$ and $T_{flow}$ in step 320. The result is three pairs of values for the speed of sound and density. (S1, $\rho$1), (S2, $\rho$2) and (S3, $\rho$3) corresponding to the three pure hydrocarbon gas mixtures $G_1$, G2, and G3 at the measured $P_{flow}$ and $T_{flow}$.

In step 330, the variation of density with speed of sound for a pure hydrocarbon natural gas mixture is modeled using a second order (quadratic) equation. The form of the equation is:

$$\rho_{PH} = AP + \frac{BP}{S} + \frac{CP}{S^2} \quad [1\text{-}18]$$

The values of the coefficients, AP, BP, and CP are determined from the values of (S1,$\rho$1), (S2,$\rho$2) and (S3,$\rho$3) derived in step 320. The variation in molecular weight of the pure hydrocarbon natural gas mixtures as a function of speed of sound is also modeled as a second order equation. The form of this equation is:

$$MW_{PH} = AMW + \frac{BMW}{S} + \frac{CMW}{S^2} \quad [1\text{-}19]$$

The values of the coefficients AMW, BMW and CMW are then determined using the known/derived values of(MW1, S1), (MW2,S2) and (MW3,S3) for the gas mixtures $G_1$, $G_2$, and $G_3$. The molecular weight values were calculated in step 305. The fully determined equations [1-18] and [1-19] now provide a mechanism to calculate the density and the molecular weight of a natural gas mixture that does not contain diluents, specifically, nitrogen and carbon dioxide To account for the effect of natural gas diluents on natural gas density and the gas mixture molecular weight, additional property data representative of mixtures containing nitrogen and carbon dioxide must be developed. Therefore, six dilute gas mixtures based upon varying the compositions of the pure hydrocarbon mixtures identified as ID#40_00_00=$G_1$, Gas ID#26_00_00=$G_2$, and Gas ID#49_00_00=$G_3$ are selected in step 340. For example, using the gas mixture designated Gas ID#40_00_00, the concentration of each hydrocarbon gas component in the Table 1 ID# 40 gas mixture can be miltiplied by factor of 0.94, and 2.0 mole % of carbon dioxide and 4.0 mole % of nitrogen can be added to form a new (dilute) gas mixture, designated as Gas ID#40_02_04=$G_4$. Another gas mixture can be formed by replacing the 2.0 mole % of carbon dioxide with 4.0 mole % of carbon dioxide, and the 4.0 mole % of nitrogen with 2.0 mole % of nitrogen (using the same multiplication factor 0.94). This produces a new dilute gas mixture identified as Gas ID#40_04_02=G5. In a similar manner, four more gas mixtures identified as Gas ID#26_02_04=G6, Gas ID#26_04_02=G7, Gas ID#49_02_04=G8, and Gas ID#49_04_02$G_9$ can be formulated. The molecular weights for these six new gas mixtures can be calculated using standard methods, well known in the art. The resulting values of MW for the mixtures G4, G5, G6, G7, G8, and $G_9$ are MW4=17.230, MW5=17.550, MW6=18.280, MW7=18.600, MW8=19.876 and MW9=20.196, respectively.

In step 360, an existing commercial computer code (similar or identical to SonicWare™ software) is used to calculate values of the gas mixture density, $\rho$, and the speed of sound, S, over a range of values for gas temperature, T, and gas pressure, P, for the gas mixtures $G_4$, $G_5$, $G_6$, $G_7$, $G_8$, and $G_9$ (similar to the process described for step 310). The values of $\rho$, S, T, and P are then saved as property data files in the processor 80 memory, such as PROPS4. DAT, PROPS5.DAT, PROPS6.DAT, PROPS7.DAT, PROPS8.DAT and PROPS9.DAT.

Similarly to the process of step 320, the properties for gas mixtures $G_4$, $G_5$, $G_6$, $G_7$, $G_8$, and $G_9$ stored as PROPS4.DAT, PROPS5.DAT, PROPS6.DAT, PROPS7.DAT, PROPS8.DAT and PROPS9.DAT are used to provide numerical fits for density and speed of sound as functions of temperature and pressure in the vicinity of the measured $P_{flow}$ and $T_{flow}$ using a cubic-spline fit algorithm in step 370. Then the cubic spline fit program is used to calculate six pairs of speed of sound and gas mixture density values (S4,$\rho$4), (S5,$\rho$5), (S6,$\rho$6), (S7,$\rho$7), (S8,$\rho$8) and (S9, $\rho$9) corresponding to the diluted gas mixtures $G_4$, $G_5$, $G_6$, $G_7$, $G_8$, and $G_9$.

The model equations for $\rho_{PH}$ and $MW_{PH}$ are modified in step 380 to include the effect of the natural gas diluents N2 and CO2. The new form of the equation for $\rho$ is:

$$\rho_{dil} = \left(AP + \frac{BP}{S} + \frac{CP}{S^2}\right) * \quad [1\text{-}20]$$
$$\left(1 + \left(D1 + \frac{D2}{S} + \frac{D3}{S^2}\right) * XCO_2 + \left(E1 + \frac{E2}{S} + \frac{E3}{S^2}\right) * XN_2\right)$$

where $XCO_2$ is the mole % of carbon dioxide and $XN_2$ is the mole % of nitrogen. The values of AP, BP and CP were determined in step 330. The six new coefficients, D1, D2, D3 and E1, E2 and E3 can be calculated by substituting the pairs of values (S4, $\rho$4) through (S9, $\rho$9) into this equation and using matrix algebra operations to solve the six simultaneous equations for the coefficients. The resulting fully-determined equation models the variation of dilute natural gas density as a function of temperature, pressure, speed of sound, mole % of carbon dioxide, and mole % of nitrogen measured at flowing pressure and temperature.

Similarly, an equation for molecular weight as a function of the speed of sound and the mole % concentrations of carbon dioxide and nitrogen can be formed as follows:

$$MW_{dil} = \left(AMW + \frac{BMW}{S} + \frac{CMW}{S^2}\right) * \quad [1\text{-}21]$$
$$\left(1 + \left(DM1 + \frac{DM2}{S} + \frac{DM3}{S^2}\right) * XCO_2 + \right.$$
$$\left. \left(EM1 + \frac{EM2}{S} + \frac{EM3}{S^2}\right) * XN_2 \right)$$

The values of coefficients AMW, BMW and CMW were determined in step 330. The six new coefficients, DM1, DM2, DM3, EM1, EM2 and EM3 can be calculated by substituting the pairs of values (S4, MW4) through (S9, MW9) into equation [1-21] and using matrix algebra operations to solve the six simultaneous equations. The fully-determined equation [1-21] models the variation of a natural gas mixture that includes diluents as a function of temperature, pressure, the speed of sound, the mole % concentration of carbon dioxide, and mole % concentration of nitrogen, measured at flowing pressure and temperature.

Instead of measuring the speed of sound $S_{std}$ at standard pressure and temperature as described previously, it is now calculated in step 390. The values of MW for the nine natural gas mixtures (three without diluents, and six with diluents) were determined in steps 305 and 340. An existing commercial computer code (similar or identical to SonicWare™ software) is used to calculate the speed of sound and the density for each of the nine natural gas mixtures without diluents, $G_1 \ldots G_9$ at standard pressure and temperature. The values of AMW, BMW and CMW are determined as in step 330, except that the newly-determined sound speed values are used for the natural gas mixtures without diluents, $G_1$, $G_2$ and $G_3$. Values for DM1, DM2, DM3, EM1, EM2 and EM3 can then be determined as in step 380 using the newly-determined sound speed values for the six natural gas mixtures with diluents, $G_4$, $G_5$, $G_6$, $G_7$, $G_8$, and $G_9$. Finally, the value of molecular weight determined in Step 380 is set equal to the model equation [1-21] using the coefficients calculated with the newly-determined sound speed values. The resulting equation can be solved iteratively for the standard sound speed at standard temperature and pressure for the gas mixture of unknown composition.

With the value of the standard sound speed now determined, together with the mole % concentrations of carbon dioxide, $X_{CO2}$, and nitrogen, $X_{N2}$, the inferential correlation equation [1-10] can be used to calculate the mass-based heating value, $H_m$, in units of Btu/lbm, at step 410. The energy flow rate can be calculated by multiplying the value of the mass-based heating value Hm by the natural gas mixture density derived in step 380, and the gas volumetric flow rate, as measured by a conventional flow meter. Since natural gas transmission companies prefer reporting the energy content of natural gas in units of Btu/standard cubic feet of volume, this quantity can be calculated as the product of the mass-based heating value Hm multiplied by the "standard" density, $\rho_{std}$, which is in turn calculated using the inferential correlation equation [1-11].

Many variations and modifications may be made to the disclosed embodiments of the invention without departing from the spirit and principles described herein. All such modifications and variations are intended to be included within the scope of the present invention, as defined by the following claims.

What is claimed is:

1. A system to determine a heating value of a gas having a plurality of components, comprising:
   a database storing data representing a number of gas mixtures with known gas compositions;
   a sound velocity measurement device adapted to determine a speed of sound in the gas;
   a concentration measurement device adapted to determine the concentration of two or more diluent components of the gas, thereby providing diluent concentration measurements; and
   a processor system that stores values representing the speed of sound and the diluent concentration measurements as gas characterization properties and that calculates said heating value by calculating the mixture molecular weight as a function of the speed of sound and the diluent concentration values; calculating the hydrocarbon molecular weight as the difference between the mixture molecular weight and the molecular weight of the diluent concentrations, and calculating the heating value as a function of the hydrocarbon molecular weight and a set of constant values, wherein the constant values are determined from the gas characterization properties and by statistical analysis of data in the database.

2. The system of claim 1, wherein the set of concentration measurements includes a measurement of carbon dioxide concentration and a measurement of nitrogen concentration.

3. The system of claim 1, wherein the speed of sound is determined at standard temperature and standard pressure of the gas.

4. The system of claim 1, wherein the heating value is a mixture molar ideal gross heating value.

5. The system of claim 1, wherein the heating value is a mass-based heating value.

6. The system of claim 1, wherein the sound velocity measurement device operates by directly measuring the speed of sound in the gas.

7. The system of claim 1, wherein the concentration measurement device operates by directly measuring the concentration of at least a selected one of the diluent components.

8. The system of claim 1, wherein the concentration measurement device correlates a thermodynamic property of a selected one of the diluent components and one or more directly measurable inferential properties of that component to provide the concentration of that component.

9. The system of claim 5, further comprising the steps of equating the density of the gas to the mixture molecular weight and calculating the standard heating value as the product of the mass based heating value and the density.

10. The system of claim 9, further comprising the steps of measuring the flow rate of the gas and calculating the energy flow rate as the product of the standard heating value and the flow rate to determine an energy flow rate of the gas.

11. A method to determine a heating value of a gas having a plurality of components, comprising the steps of: determining a speed of sound in the gas;
   determining the concentration measurements of two or more diluent components of the gas;
   storing the speed of sound and the diluent concentration measurements as a set of gas characterization properties; and
   calculating said heating value by calculating the mixture molecular weight as a function of the speed of sound and a first set of constant values; calculating the hydrocarbon molecular weight as the difference between the mixture molecular weight and the molecular weight of the diluent concentrations, and calculating the heating value as a function of the hydrocarbon molecular weight and a second set of constant values; wherein the constant values are determined from the known gas characterization values and by statisical analysis of data representing a number of gas mixtures and their gas compositions.

12. The method of claim 11, wherein the diluent concentration measurements include a measurement of carbon dioxide concentration and a measurement of nitrogen concentration.

13. The method of claim 11, wherein the speed of sound is determined at standard temperature and standard pressure of the gas.

14. The method of claim 11, wherein the heating value is a mixture molar ideal gross heating value.

15. The method of claim 11, wherein the heating value is a mass-based heating value.

16. The system of claim 11, wherein the step of determining the speed of sound includes the step of directly measuring the speed of sound in the gas.

17. The method of claim 11, wherein the step of determining the concentration measurements includes the step of directly measuring concentration of one of the diluent components.

18. The method of claim 11, wherein the step of determining the concentration measurements includes the step of correlating a thermodynamic property of a selected one of the diluent components and one or more directly measurable inferential properties of that component.

19. The method of claim 11, further comprising the steps of equating the density of the gas to the mixture molecular weight and calculating the standard heating value as the product of the mass based heating value and the density.

20. The method of claim 19, further comprising the steps of measuring the flow rate of the gas and calculating the energy flow rate as the product of the standard heating value and the flow rate to determine an energy flow rate of the gas.

21. A method to determine the mixture molecular weight of a gas having a plurality of components, comprising the steps of:

determining a speed of sound in the gas;

determining the concentration measurements of two or more diluent components of the gas;

calculating said mixture molecular weight as a function of the speed of sound, the diluent concentration values, and a set of constant values, wherein the constant values are determined by statistical analysis of data representing a number of gas mixtures having known component concentrations.

22. The method of claim 21, wherein the diluent concentration measurements include a measurement of carbon dioxide concentration and a measurement of nitrogen concentration.

23. The method of claim 21, wherein the speed of sound is determined at standard temperature and standard pressure of the gas.

24. The method of claim 21, wherein the function is a quadratic function.

25. A method to determine the standard density of a gas having a plurality of components, comprising the steps of: determining a speed of sound in the gas; determining the concentration measurements of two or more diluent components of the gas;

calculating said density as a function of the speed of sound, the diluent concentration values, and a set of constant values, wherein the constant values are determined by statistical analysis of data representing a number of gas mixtures having known component concentrations.

26. The method of claim 25, wherein the diluent concentration measurements include a measurement of carbon dioxide concentration and a measurement of nitrogen concentration.

27. The method of claim 25, wherein the speed of sound is determined at standard temperature and standard pressure of the gas.

28. The method of claim 25, wherein the function is a quadratic function.

* * * * *